US012653722B2

(12) United States Patent
 Locke

(10) Patent No.: US 12,653,722 B2
(45) Date of Patent: Jun. 16, 2026

(54) DEFORMABLE DRESSING FOR NEGATIVE-PRESSURE THERAPY

(71) Applicant: KCI Manufacturing Unlimited Company, Westmeath (IE)

(72) Inventor: Christopher Brian Locke, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 418 days.

(21) Appl. No.: 18/039,488

(22) PCT Filed: Nov. 16, 2021

(86) PCT No.: PCT/IB2021/060593
§ 371 (c)(1),
(2) Date: May 30, 2023

(87) PCT Pub. No.: WO2022/123359
PCT Pub. Date: Jun. 16, 2022

(65) Prior Publication Data
US 2024/0000617 A1     Jan. 4, 2024

Related U.S. Application Data

(60) Provisional application No. 63/122,380, filed on Dec. 7, 2020.

(51) Int. Cl.
| *A61F 13/00* | (2024.01) |
| *A61F 13/0203* | (2024.01) |
| *A61F 13/05* | (2024.01) |

(52) U.S. Cl.
CPC ............ *A61F 13/05* (2024.01); *A61F 13/022* (2013.01); *A61F 2013/00578* (2013.01)

(58) Field of Classification Search
None
See application file for complete search history.

(56) References Cited

U.S. PATENT DOCUMENTS

| 1,355,846 A | 10/1920 | Rannells |
| 2,547,758 A | 4/1951 | Keeling |
| | (Continued) | |

FOREIGN PATENT DOCUMENTS

| AU | 550575 B2 | 3/1986 |
| AU | 745271 B2 | 3/2002 |
| | (Continued) | |

OTHER PUBLICATIONS

International Search Report and Written Opinion for PCT International Application No. PCT/IB2021/060593, mailed Feb. 25, 2022.

(Continued)

*Primary Examiner* — Kim M Lewis

(57) ABSTRACT

A dressing for treating a tissue site with negative pressure may have, in a relaxed state in which no external forces are applied to the dressing, both a first non-planar surface and a second non-planar surface opposite the first non-planar surface. The dressing may include a fluid management layer comprising a polymer film and a plurality of fluid restrictions extending through the polymer film and configured to deform. The dressing may also include a manifold layer coupled to the fluid management layer.

23 Claims, 10 Drawing Sheets

(56)     References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,794,554 | B2* | 9/2004 | Sessions ........... A61F 13/01021 |
| | | | 604/290 |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2007/0027414 | A1* | 2/2007 | Hoffman ............... A61M 1/915 |
| | | | 602/2 |
| 2010/0174250 | A1 | 7/2010 | Hu et al. |
| 2011/0201715 | A1 | 8/2011 | Schoenberger et al. |
| 2014/0163491 | A1 | 6/2014 | Schuessler et al. |
| 2015/0080788 | A1 | 3/2015 | Blott et al. |
| 2018/0353336 | A1 | 12/2018 | Locke et al. |
| 2018/0353665 | A1 | 12/2018 | Locke et al. |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |

(56)         References Cited

FOREIGN PATENT DOCUMENTS

| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2010147930 A1 | 12/2010 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Japanese Office Action for corresponding application 2023-534123, dated Aug. 19, 2025.
Chinese Office Action for corresponding application 2021800796230, dated Feb. 6, 2026.

* cited by examiner

205

205

902    901

DEFORMABLE DRESSING FOR NEGATIVE-PRESSURE THERAPY

CROSS-REFERENCE TO RELATED APPLICATIONS

This application claims the benefit of priority to U.S. Provisional Application No. 63/122,380, filed on Dec. 7, 2020, which is incorporated herein by reference in its entirety.

TECHNICAL FIELD

The invention set forth in the appended claims relates generally to tissue treatment systems and more particularly, but without limitation, to dressings and systems for tissue treatment with negative pressure and methods of using dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

In some embodiments, a dressing characterized as exhibiting decreased tensile strength, increased flexure, and/or improved conformability with respect to a tissue site may be advantageously employed in the provision of negative-pressure therapy. For example, the increased flexure and/or improved conformability of the dressing may provide for better contact between the tissue site and a tissue site-facing surface of the dressing. The improved contact between the dressing and the tissue site may have the effect of inducing micro-strain across substantially all of the tissue site, whereby cells across the tissue site experience strain, improving the outcome of the negative-pressure therapy.

In some embodiments, a dressing may be characterized as exhibiting increased flexure after a thermoforming process and/or as a result of the thermoforming process. For example, the dressing may be characterized as exhibiting increased flexure in comparison to an otherwise similar dressing that has not been thermoformed.

Additionally or alternatively, in some embodiments, a dressing may be characterized as exhibiting improved conformability with respect to a tissue site after the thermoforming process and/or as a result of the thermoforming process. For example, the dressing may be characterized as exhibiting improved conformability with respect to a tissue site in comparison to an otherwise similar dressing that has not been thermoformed.

For example, in some embodiments, a dressing for treating a tissue site with negative pressure may have, in a relaxed state in which no external forces are applied to the dressing, both a first non-planar surface and a second non-planar surface opposite the first non-planar surface. The dressing may comprise a fluid management layer comprising a polymer film and a plurality of fluid restrictions extending through the polymer film and configured to deform. The dressing may also comprise a manifold layer coupled to the fluid management layer.

Also, for example, is a method for forming a dressing for treatment of a tissue site with negative pressure. The dressing formed by the method may comprise a fluid management layer comprising a polymer film and a plurality of fluid restrictions extending through the polymer film and configured to deform. The dressing formed by the method may also comprise a manifold layer coupled to the fluid management layer. The method may comprise heating the fluid management layer and the manifold layer and while heated, conforming the fluid management layer and the manifold layer to a form. The method may impart to the dressing, in a relaxed state in which no external forces are applied to the dressing, both a first non-planar surface and a second non-planar surface opposite the first non-planar surface.

Also, for example, a system for treating a tissue site may comprise a dressing for treating a tissue site with negative pressure. The dressing may have, in a relaxed state in which no external forces are applied to the dressing, both a first non-planar surface and a second non-planar surface opposite the first non-planar surface. The dressing may comprise a fluid management layer comprising a polymer film and a plurality of fluid restrictions extending through the polymer film and configured to deform and a manifold layer coupled to the fluid management layer. The system may also comprise a negative-pressure source configured to be fluidly coupled to the dressing.

Also, for example, a dressing for treating a tissue site with negative pressure may comprise a fluid management layer comprising a polymer film and a plurality of fluid restrictions extending through the polymer film and configured to deform. The dressing may also comprise a manifold layer coupled to the fluid management layer. The dressing may be formed by a thermoforming process comprising heating the fluid management layer and the manifold layer and, while heated, conforming the fluid management layer and the manifold layer to a form. At least a portion of the dressing may exhibit a decrease in tensile strength as a result of the thermoforming process.

Also, for example, is a method for forming a dressing for treatment of a tissue site with negative pressure. The dressing formed by the process may comprise a fluid management layer comprising a polymer film and a plurality of fluid restrictions extending through the polymer film and configured to deform and also comprising a manifold layer coupled to the fluid management layer. The method may comprise heating the fluid management layer and the manifold layer and, while heated, conforming the fluid management layer and the manifold layer to a form. At least a portion of the dressing may exhibit a decrease in tensile strength as a result of the thermoforming process.

Also, for example, a system for treating a tissue site may comprise a dressing. The dressing may comprise a fluid management layer comprising a polymer film and a plurality of fluid restrictions extending through the polymer film and configured to deform and a manifold layer coupled to the fluid management layer. The dressing may be formed by a thermoforming process comprising heating the fluid management layer and the manifold layer and, while heated, conforming the fluid management layer and the manifold layer to a form. At least a portion of the dressing may exhibit a decrease in tensile strength as a result of the thermoforming process. The system may also comprise a negative-pressure source configured to be fluidly coupled to the dressing.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
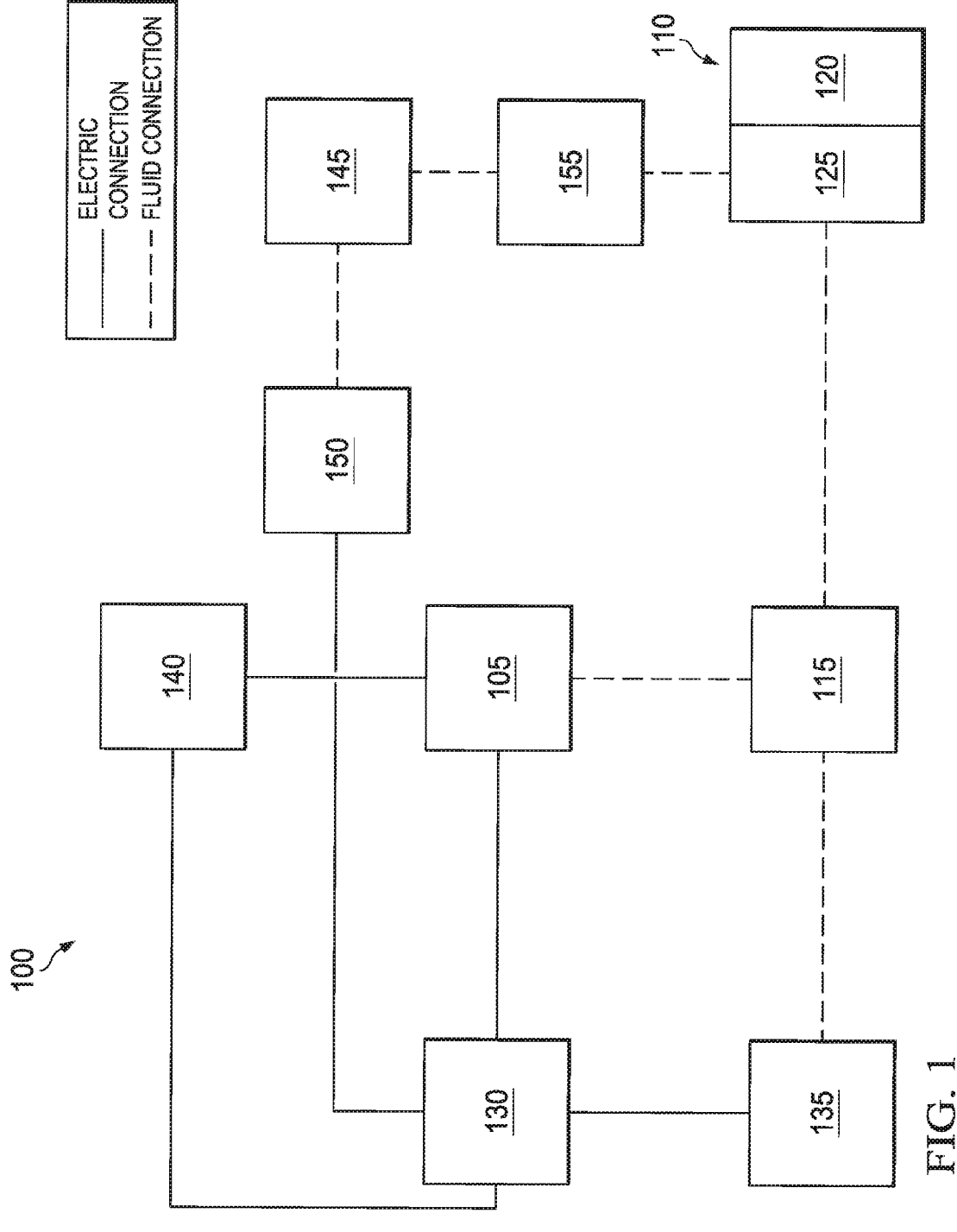
FIG. 1 is a block diagram of an example embodiment of a therapy system that can provide negative-pressure treatment and instillation treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source 145 during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may include or may be a manifold. A manifold in this context may comprise a means for collecting or distributing fluid relative to a tissue site under pressure. For example, a manifold may be adapted to receive negative pressure from a source and distribute negative pressure through multiple apertures, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or be formed from a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or be formed from, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, a Tegaderm® drape, commercially available from 3M Company, Minneapolis, Minnesota; polyurethane (PU) drape, commercially available from Avery Dennison Corporation, Pasadena, California; polyether block polyamide copolymer (PEBAX), for example, from Arkema S. A., Colombes, France;

and Inspire 2301 and Inspire 2327 polyurethane films, commercially available from Exopack Advanced Coatings, Wrexham, United Kingdom. In some embodiments, the cover 125 may comprise Inspire 2301 having an MVTR (upright cup technique) of 2600 grams per square meter per twenty-four hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

In general, exudate and other fluid flow toward lower pressure along a fluid path. Thus, the term "downstream" typically may refer to a location in a fluid path relatively closer to a source of negative pressure or further away from a source of positive pressure. Conversely, the term "upstream" may refer to a location relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in the container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, the controller 130 may include an input device for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
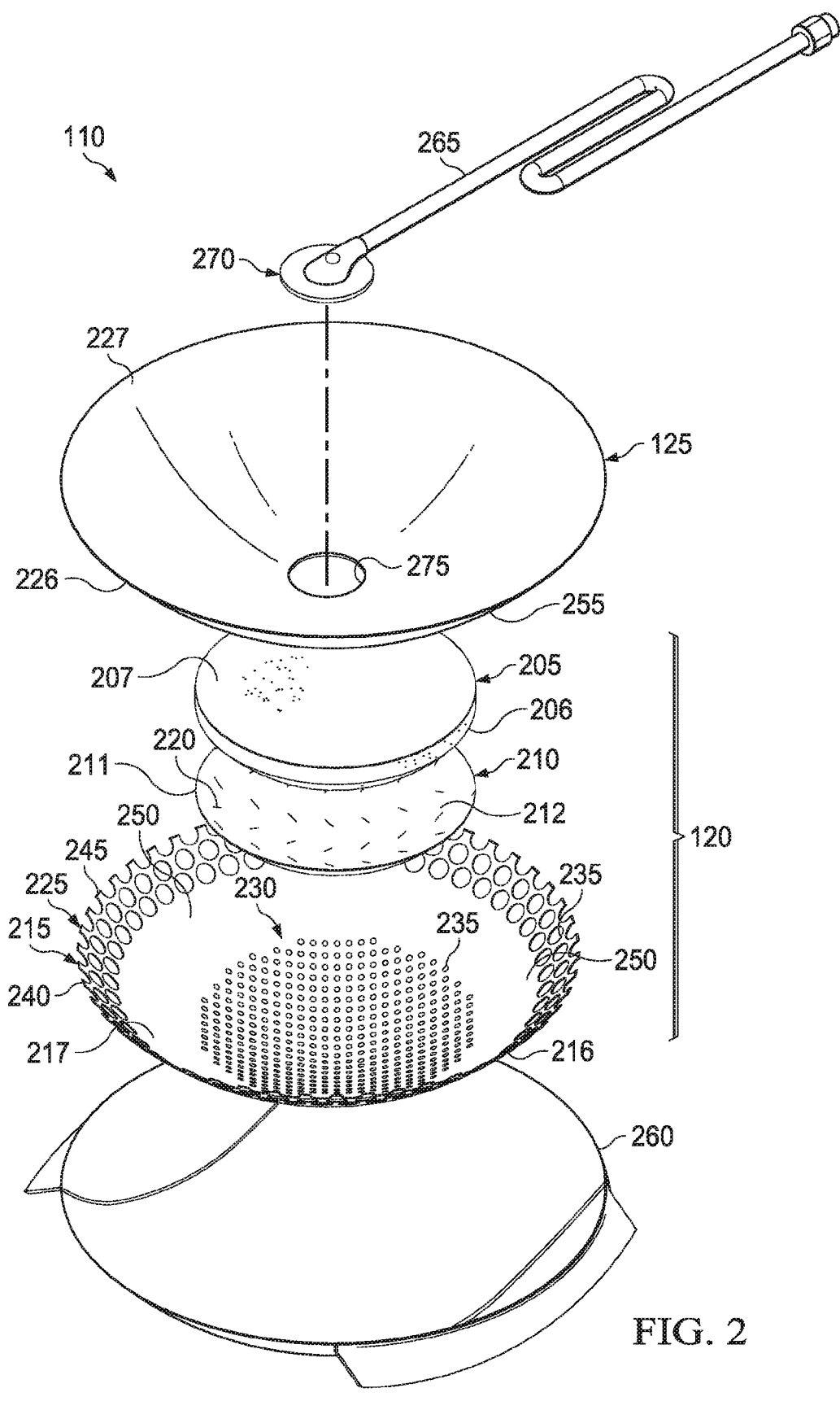
FIG. 2 is an exploded view of an example of a dressing, illustrating additional details that may be associated with some example embodiments of the therapy system of FIG. 1.

FIG. 2 is an exploded view of an example of the dressing 110 of FIG. 1, illustrating additional details that may be associated with some embodiments in which the tissue interface 120 comprises more than one layer. In the embodiment of FIG. 2, the tissue interface 120 includes a plurality of layers, for example, a first layer, a second layer, and a third layer. More particularly, in the example of FIG. 2, the tissue interface 120 comprises a manifold layer 205, a fluid management layer 210, and a contact layer 215. In some embodiments, the manifold layer 205 may be disposed adjacent to the fluid management layer 210, and the contact layer 215 may be disposed adjacent to the fluid management layer 210 opposite the manifold layer 205. For example, the manifold layer 205, the fluid management layer 210, and the contact layer 215 may be stacked so that the manifold layer 205 is in contact with the fluid management layer 210, and the fluid management layer 210 is in contact with the manifold layer 205 and the contact layer 215. One or more of the manifold layer 205, the fluid management layer 210, and the contact layer 215 may also be bonded to an adjacent layer in some embodiments.

In some embodiments, the manifold layer 205 may be characterized with respect to a length, a width, and a thickness extending between the length and the width or between opposing surfaces of the manifold layer 205. Likewise, the fluid management layer 210 may be characterized with respect to a length, a width, and a thickness extending between the length and the width or between opposing surfaces of the fluid management layer 210. Also, the contact layer 215 may be characterized with respect to a length, a width, and a thickness, extending between the length and the width or between opposing surfaces of the contact layer 215.

In some embodiments, the thickness of the fluid management layer 210 may be substantially constant across the length and width of the manifold layer 205. Also, the manifold layer 205 may include a first surface 206 and a second surface 207, the fluid management layer 210 may include a third surface 211 and a fourth surface 212, and the contact layer 215 may include a fifth surface 216 and a sixth surface 217. In some embodiments, one or more of the first surface 206, the second surface 207, the third surface 211, the fourth surface 212, the fifth surface 216, and the sixth surface 217 may be generally characterized as nonplanar surfaces. For example, generally recognizable as having one or more undulations and/or deviations from a single geometric plane.

For example, in some embodiments, one or more of the first surface 206, the second surface 207, the third surface 211, the fourth surface 212, the fifth surface 216, and the sixth surface 217 may comprise one or more non-planar surface features. Examples of non-planar surface features may include a portion of an interior or exterior surface of a sphere, an ellipsoid, a torus, a cylinder, a paraboloid, a hyperboloid, a cone, a prism, a pyramid, or a tetrahedron. In some embodiments, three of the first surface 206, the second surface 207, the third surface 211, the fourth surface 212, the fifth surface 216, and the sixth surface 217 may be characterized as generally convex and the other three of the first surface 206, the second surface 207, the third surface 211, the fourth surface 212, the fifth surface 216, and the sixth surface 217 may be characterized as concave. Various surfaces of the tissue interface 120 may be configured to extend into and/or at least partially fill a tissue site that has a depth extending beneath the surface of the tissue, for example, a deep wound. In some embodiments, such as illustrated in the embodiment of FIG. 2, the first surface 206, the third surface 211, and the fifth surface 216 may be characterized as generally convex or as having predominantly convex surface features and, likewise, the second surface 207, the fourth surface 212, and the sixth surface 217 may be characterized as generally concave or as having predominantly concave surface features. For example, both the first surface 206 and the third surface 211 may comprise at least one outward-facing curvature and, likewise, both the second surface 207 and the fourth surface 212 comprise at least one inward-facing curvature. In some embodiments, these curvatures may be substantially constant over the length of the dressing 110, the width of the dressing 110, or both. Additionally or alternatively, these curvatures may vary over the length of the dressing 110, the width of the dressing 110, or both.

In some embodiments, the curvature exhibited by the first surface 206, the second surface 207, the third surface 211, or the fourth surface 212 may be such that a respective surface deviates from planar by at least about 50% of the combined thicknesses of the layers of the dressing 110, or by about the combined thicknesses of the layers of the dressing 110, or by at least about 125% of the combined thicknesses of the layers of the dressing 110, or by at least about 150% of the combined thicknesses of the layers of the dressing 110, or by at least about 175% of the combined thicknesses of the layers of the dressing 110, or by at least about 200% of the combined thicknesses of the layers of the dressing 110, or by at least about 225% of the combined thicknesses of the layers of the dressing 110, or by at least about 250% of the combined thicknesses of the layers of the dressing 110, or by at least about 275% of the combined thicknesses of the layers of the dressing 110, or by at least about 300% of the combined thicknesses of the layers of the dressing 110. For example, the curvature exhibited by the first surface 206, the second surface 207, the third surface 211, or the fourth surface 212 may be such that a respective surface exhibits a change in elevation between two points on the respective surfaces of at least about 50% of the combined thicknesses of the layers of the dressing 110, or about the combined thicknesses of the layers of the dressing 110, or at least about 125% of the combined thicknesses of the layers of the dressing 110, or at least about 150% of the combined thicknesses of the layers of the dressing 110, or at least about 175% of the combined thicknesses of the layers of the dressing 110, or at least about 200% of the combined thicknesses of the layers of the dressing 110, or at least about 225% of the combined thicknesses of the layers of the dressing 110, or at least about 250% of the combined thicknesses of the layers of the dressing 110, or at least about 275% of the combined thicknesses of the layers of the dressing 110, or at least about 300% of the combined thicknesses of the layers of the dressing 110.

In some embodiments, for example, where the tissue site intended for treatment has a depth extending beneath the surface of the tissue, the tissue interface 120 may be configured to allow the convex surfaces to face the tissue site. For example, in the context of FIG. 2, the first surface 206 and the third surface 211 may extend into and at least partially fill a void in the tissue site when the tissue interface 120 is placed with respect to the tissue site.

The manifold layer 205 may generally comprise a means for collecting or distributing fluid across the tissue interface 120 under pressure, for example, the manifold layer 205 may be adapted to receive negative pressure from a source and distribute negative pressure. In some embodiments, the manifold layer 205 may comprise or be formed from a reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the manifold layer 205 may also vary according to needs of a prescribed therapy. The 25% compression load deflection of the manifold layer 205 may be at least 0.35 pounds per square inch, and the 65% compression load deflection may be at least 0.43 pounds per square inch. In some embodiments, the tensile strength of the manifold layer 205 may be at least 10 pounds per square inch. The manifold layer 205 may have a tear strength of at least 2.5 pounds per inch. In some embodiments, the manifold layer 205 may be foam comprised of polyols such as polyester or polyether, isocyanate such as toluene diisocyanate, and polymerization modifiers such as amines and tin compounds. In some examples, the manifold layer 205 may be reticulated polyurethane foam such as found in a V.A.C.® GRANUFOAM™ Dressing or a V.A.C.® VERAFLO™ Dressing, both available from Kinetic Concepts, Inc. of San Antonio, Texas.

Alternatively, in some embodiments, the manifold layer 205 may comprise a closed-cell foam. For example, in some embodiments, the manifold layer 205 may comprise an expanded foam, for example, a foam formed from a process by which comprises expansion of a foam precursor material. For example, in some embodiments, an expanded foam may be formed from a process comprising extrusion of a polymeric material, impregnation of the polymeric material with an inert gas at high heat and pressure to form an impregnated polymeric material, and expansion of the impregnated polymeric material to form the expanded foam material.

During the extrusion step, raw polymeric material may be melted and forced through a die to form a generally continuous stock material, for example, the extruded polymeric material. The polymeric material may comprise any suitable polymer, copolymer, or combination thereof, dependent upon the needs of a prescribed therapy. For example, in various embodiments, the polymeric material comprises cross-linked ethylene-vinyl acetate copolymer, a cross-linked polyolefin, for example, cross-linked polyethylene, or a cross-linked ethyl-methyl-acrylate copolymer.

In some embodiments, the polymeric material may have one or more additives or modifiers incorporated in an amount sufficient to impart a desired effect during the extrusion step. For example, in some embodiments, an antimicrobial material may be incorporated within the polymeric material during extrusion. Suitable examples of an antimicrobial material include a metal, such as silver, which may be present in metallic form, in ionic form (e.g., a silver salt), or both. In some embodiments, silver may be present in combination with one or more additional metals, for example, gold, platinum, ferro-manganese, copper, zinc, or combinations thereof. In some examples, silver may be incorporated into the polymeric material in an amount from about 1% to about 10% by weight of the polymeric material. Additionally or alternatively, in some embodiments, a super-absorbent polymer (SAP) may be incorporated within the polymeric material during extrusion. Generally, relative to their mass, SAPs can absorb and retain large quantities of liquid, and in particular, water. Many medical disposables, such as canisters and dressings, use SAPs to hold and stabilize or solidify wound fluids. The SAPs may be of the type often referred to as "hydrogels," "super-absorbents," or "hydrocolloids." For example, SAPs may absorb liquids by bonding with water molecules through hydrogen bonding. In some examples, a SAP may be incorporated into the polymeric material in an amount from about 10% to about 20% by weight of the polymeric material.

During the impregnation step, the polymeric material is exposed to an inert gas under elevated heat and pressure, causing the inert gas to permeate the polymeric material. The inert gas may comprise nitrogen gas, for example, at least 90% nitrogen gas, or at least 95% nitrogen gas, or at least 99% nitrogen gas, by weight. The parameters associated with the impregnation step, for example, the temperature, partial pressure of the inert gas and the duration of the impregnation, may be manipulated to alter the properties of the impregnated polymeric material and, accordingly, the properties of the resultant expanded foam.

During the expansion step, the impregnated polymeric material is subjected to heat under pressure in the presence of a reduced pressure, for example, a pressure that is less than the pressure employed during the impregnation step. In some embodiments, the impregnated polymeric material may be expanded in a low-pressure autoclave. Not intending to be bound by theory, during the expansion step, the reduction in pressure may allow the inert gas to expand, causing the formation of pores or cells within the expanded polymeric material. The parameters associated with the expansion step, for example, the temperature, pressure, and the duration of the expansion, may be manipulated to alter the properties of the expanded polymeric material, the expanded foam.

In some embodiments, a closed-cell foam such as an expanded foam may comprise a plurality of pores or cells that can be generally characterized as not being interconnected. In some embodiments, an expanded foam may be characterized as resilient such that in the presence of a negative pressure, the expanded foam exhibits a resistance to compression, for example, a resistance to compression that is relatively high in comparison to an open-cell foam. The resistance to compression exhibited by the expanded foam may be dependent upon, among other parameters, the density of the expanded foam and the hardness of the material forming the expanded foam, as well as the closed-cell nature of the expanded foam. For example, the expanded foam may be characterized as having a density of from about 0.04 $g/cm^3$ to about 0.06 $g/cm^3$ according to ISO 7214:2012, or from about 0.045 $g/cm^3$ to about 0.055 $g/cm^3$, about 0.05 $g/cm^3$. Additionally, the expanded foam may be characterized as having a Shore Hardness on the OO Scale of from about 40 to 55 according to ISO 868:2003, or from about 42 to about 48, or about 46. In some embodiments, the expanded foam may be characterized as exhibiting a compression stress-strain at 25% compression of about 39 for a 25 mm cell-cell according to ISO 7214:2012 and/or a compression stress-strain at 50% compression of about 100 for a 25 mm cell-cell according to ISO 7214:2012.

In some embodiments, the manifold layer 205 may comprise a closed-cell cross-linked polyolefin foam such as one of the AZOTE® range of foams available from Zotefoams Plc, of London, England. In various non-limiting examples, the manifold layer 205 may be a closed-cell cross-linked polyethylene foam such as one of the Plastazote® line of foams, a closed-cell cross-linked ethylene copolymer foam such as one of the Evazote® line of foams, or a closed-cell, cross-linked ethylene copolymer foam such as one of the Supazote® line of foams, all available from Zotefoams Plc, of London, England. In a particular example embodiment, the manifold layer 205 may be a closed-cell cross-linked ethylene copolymer foam as Evazote® EV50.

In some embodiments, the manifold layer 205 may comprise one or more apertures. For example, in some embodiments, the manifold layer 205 may include a plurality of collapsible apertures extending at least partially into the thickness from either the first surface 206 or the second surface 207. The collapsible aperture may be generally configured to exhibit a relatively high degree of deformation in response to a negative pressure applied to the manifold layer 205. For example, the collapsible apertures may be configured to exhibit a relatively high percentage change in the area of a cross-section in a plane parallel to either the first surface 206 or the second surface 207. In some embodiments, the collapsible apertures may be effective to allow the manifold layer 205 to exhibit radial collapse, for example, to exhibit a deformation of the manifold layer 205 or a portion thereof such that the manifold layer 205 exhibits a decrease in at least one dimension of the first surface 206 and/or the second surface 207 relative to that dimension when the manifold layer 205 is not subjected to negative pressure (e.g., a nominal or relaxed length and/or a nominal or relaxed width). In some embodiments, the radial collapse exhibited by the manifold layer 205 may be determined by various factors related to, for example, the dimensions of the collapsible apertures.

Additionally or alternatively, in some embodiments, the manifold layer 205 may comprise a plurality of fluid apertures extending through the thickness between the first surface 206 and the second surface 207. The fluid apertures may generally refer to an aperture generally configured to exhibit a relatively low degree of deformation in response to a negative pressure applied to the manifold layer 205, for example, to exhibit a relatively low percentage change in a cross-section in a plane parallel to either the first surface 206 or the second surface 207. Generally, the fluid apertures may be configured to remain open to allow for the communication of a fluid between the first surface 206 and the second surface 207. In some embodiments, such as when the manifold layer 205 comprises a closed-cell foam, the fluid apertures may provide a route of fluid communication between the first surface 206 and the second surface 207 where a route of fluid through the manifold layer 205 may be otherwise absent or insufficient.

The thickness of the manifold layer 205 may also vary according to needs of a prescribed therapy. For example, the thickness of the tissue interface 120 may be decreased to reduce tension on peripheral tissue. The thickness of the manifold layer 205 can also affect the conformability of the manifold layer 205. In some embodiments, a thickness of the manifold layer 205 in a range of about 5 millimeters to 10 millimeters may be suitable.

The fluid management layer 210 may comprise a means for controlling or managing fluid flow. In some embodiments, the fluid management layer 210 may comprise or be formed from a liquid-impermeable, elastomeric material. For example, the fluid management layer 210 may comprise or be formed from a polymer film. The fluid management layer 210 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances apart from the non-planar surface features. For example, the surface of the fluid management layer 210 may have height deviations limited to 0.2 millimeters over a centimeter.

In some embodiments, the fluid management layer 210 may be hydrophobic. The hydrophobicity of the fluid management layer 210 may vary, but may have a contact angle with water of at least ninety degrees in some embodiments. In some embodiments the fluid management layer 210 may have a contact angle with water of no more than 150 degrees. For example, in some embodiments, the contact angle of the fluid management layer 210 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things Non-limiting examples of such integrated systems may include the FTA125, FTA200, FTA2000, and FTA4000 systems, all commercially available from First Ten Angstroms, Inc., of Portsmouth, Virginia, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the fluid management layer 210 may be further enhanced with a hydrophobic coating of other materials, such as silicones and fluorocarbons, either as coated from a liquid, or plasma coated.

The fluid management layer 210 may also be suitable for welding to other layers, including the manifold layer 205. For example, the fluid management layer 210 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the fluid management layer 210 may vary according to a prescribed therapy or application. In some embodiments, an area density of less than 40 grams per square meter may be suitable, and an area density of about 20-30 grams per square meter may be particularly advantageous for some applications.

In some embodiments, the fluid management layer 210 may comprise or be formed from a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the fluid management layer 210 may have one or more fluid restrictions 220, which can be distributed uniformly or randomly across the fluid management layer 210. The fluid restrictions 220 may be bi-directional and pressure-responsive. For example, the fluid restrictions 220 can generally comprise an elastic passage that is normally unstrained to substantially reduce liquid flow, and can expand in response to a pressure gradient or deformation of the fluid management layer 210. In some embodiments, the fluid restrictions 220 may comprise perforations in the fluid management layer 210. Perforations may be formed by removing material from the fluid management layer 210. For example, perforations may be formed by cutting through the fluid management layer 210, which may also deform the edges of the perforations in some embodiments. In the absence of a pressure gradient across the perforations or deformation of the fluid management layer 210, the passages may be sufficiently small to form a seal or flow restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient or deformation of the fluid management layer 210. A fenestration in the fluid management layer 210 may be a suitable valve for some applications. Fenestrations may also be formed by removing material from the fluid management layer 210, but the amount of material removed and the resulting dimensions of the fenestrations may be an order of magnitude less than perforations, and may not deform the edges.

For example, some embodiments of the fluid restrictions 220 may comprise one or more slots or combinations of slots in the fluid management layer 210. In some examples, the fluid restrictions 220 may comprise linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications. A tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient or deformation of the fluid management layer 210 to allow increased liquid flow.

In some embodiments, the fluid restrictions 220 may be distributed across the fluid management layer 210 such that, when the fluid management layer 210 is positioned with respect to the manifold layer 205, the fluid restrictions 220 will be aligned with, overlap, in registration with, or otherwise fluidly coupled to apertures or channels within the manifold layer 205.

The optional contact layer 215 may comprise a sealing layer comprising or formed from a soft, pliable material suitable for providing a fluid seal with a tissue site. For example, the contact layer 215 may comprise, without limitation, a silicone gel, a soft silicone, hydrocolloid, hydrogel, polyurethane gel, polyolefin gel, hydrogenated styrenic copolymer gel, a foamed gel, a soft closed-cell foam such as polyurethanes and polyolefins coated with an adhesive, polyurethane, polyolefin, or hydrogenated styrenic copolymers. In some embodiments, the contact layer 215 may have a thickness between about 200 microns (μm) and about 1000 microns (μm). In some embodiments, the contact layer 215 may have a hardness between about 5 Shore 00 and about 80 Shore 00.

Further, the contact layer 215 may be comprised of hydrophobic or hydrophilic materials. In some embodiments, the contact layer 215 may be a hydrophobic-coated material. For example, the contact layer 215 may be formed by coating a spaced material, such as, for example, woven, nonwoven, molded, or extruded mesh with a hydrophobic material. The hydrophobic material for the coating may be a soft silicone, for example.

The contact layer 215 may have a periphery 225 surrounding or around an interior portion 230, and apertures 235 disposed through the periphery 225 and the interior portion 230. The interior portion 230 may correspond to a surface area of the manifold layer 205 in some examples. The contact layer 215 may also have one or more edges 245 which may form part of the periphery 225. The contact layer 215 may have an interior border 250 around the interior portion 230, disposed between the interior portion 230 and the periphery 225. The interior border 250 may be substantially free of the apertures 235, as illustrated in the example of FIG. 2. In some examples, as illustrated in FIG. 2, the interior portion 230 may be symmetrical and centrally disposed in the contact layer 215.

The apertures 235 may be formed by cutting or by application of local RF or ultrasonic energy, for example, or by other suitable techniques for forming an opening. The apertures 235 may have a uniform distribution pattern, or may be randomly distributed on the contact layer 215. The apertures 235 in the contact layer 215 may have many shapes, including circles, squares, stars, ovals, polygons, slits, complex curves, rectilinear shapes, triangles, for example, or may have some combination of such shapes.

Each of the apertures 235 may have uniform or similar geometric properties. For example, in some embodiments, each of the apertures 235 may be circular apertures, having substantially the same diameter. In some embodiments, the diameter of each of the apertures 235 may be from about 1 millimeter to about 50 millimeters. In other embodiments, the diameter of each of the apertures 235 may be from about 1 millimeter to about 20 millimeters.

In other embodiments, geometric properties of the apertures 235 may vary. For example, the diameter of the apertures 235 may vary depending on the position of the apertures 235 in the contact layer 215, as illustrated in FIG. 2. In some embodiments, the diameter of the apertures 235 in the periphery 225 of the contact layer 215 may be larger than the diameter of the apertures 235 in the interior portion 230 of the contact layer 215. For example, in some embodiments, the apertures 235 disposed in the periphery 225 may have a diameter between about 9.8 millimeters to about 10.2 millimeters. In some embodiments, the apertures 235 disposed in the interior portion 230 may have a diameter between about 1.8 millimeters to about 2.2 millimeters.

In the example of FIG. 2, the dressing 110 may further include an attachment device, such as an adhesive 255. The adhesive 255 may be, for example, a medically-acceptable, pressure-sensitive adhesive that extends about a periphery, a portion, or the entire cover 125. In some embodiments, for example, the adhesive 255 may comprise an acrylic adhesive having a coating weight between 25-65 grams per square meter (g.s.m.). Additionally or alternatively, in some embodiments, the adhesive 255 may comprise a silicone-based adhesive. Thicker adhesives, or combinations of adhesives, may be applied in some embodiments to improve the seal and reduce leaks. The adhesive 255 may be a layer having substantially the same shape as the periphery 225. In some embodiments, such a layer of the adhesive 255 may be continuous or discontinuous. Discontinuities in the adhesive 255 may be provided by apertures or holes (not shown) in the adhesive 255. The apertures or holes in the adhesive 255 may be formed after application of the adhesive 255 or by coating the adhesive 255 in patterns on a carrier layer, such as, for example, a side of the cover 125. Apertures or holes in the adhesive 255 may also be sized to enhance the MVTR of the dressing 110 in some example embodiments.

As illustrated in the example of FIG. 2, in some embodiments, a release liner 260 may be attached to or positioned adjacent to the contact layer 215, for example, to protect the adhesive 255 prior to use. The release liner 260 may also provide stiffness, such as to assist with deployment of the dressing 110. The release liner 260 may be, for example, a casting paper, a film, or polyethylene. Further, in some embodiments, the release liner 260 may be a polyester material such as polyethylene terephthalate (PET), or a similar polar semi-crystalline polymer. The use of a polar semi-crystalline polymer for the release liner 260 may substantially preclude wrinkling or other deformation of the dressing 110. For example, the polar semi-crystalline polymer may be highly orientated and resistant to softening, swelling, or other deformation that may occur when brought into contact with components of the dressing 110, or when subjected to temperature or environmental variations, or sterilization. In some embodiments, the release liner 260 may have a surface texture that may be imprinted on an adjacent layer, such as the contact layer 215. Further, a release agent may be disposed on a side of the release liner 260 that is configured to contact the contact layer 215. For example, the release agent may be a silicone coating and may have a release agent suitable to facilitate removal of the release liner 260 by hand and without damaging or deforming the dressing 110. In some embodiments, the release agent may be a fluorocarbon or a fluorosilicone, for example. In other embodiments, the release liner 260 may be uncoated or otherwise used without a release agent.

FIG. 2 also illustrates one example of a fluid conductor 265 and a dressing interface 270. As shown in the example of FIG. 2, the fluid conductor 265 may be a flexible tube, which can be fluidly coupled on one end to the dressing interface 270. The dressing interface 270 may be an elbow connector, as shown in the example of FIG. 2, which can be placed over an aperture 275 in the cover 125 to provide a fluid path between the fluid conductor 265 and the tissue interface 120.

In some embodiments, the cover 125 may include a seventh surface 226 and an eighth surface 227. As similarly disclosed with respect to the first surface 206, the second surface 207, the third surface 211, the fourth surface 212, the fifth surface 216, and the sixth surface 217, one or both of the seventh surface 226 and the eighth surface 227 may comprise one or more non-planar surface features, such as a sphere, an ellipsoid, a toms, a cylinder, a paraboloid, a hyperboloid, a cone, a prism, a pyramid, or a tetrahedron. In some embodiments, one of the seventh surface 226 and the eighth surface 227 may be characterized as generally convex and the other may be characterized as concave. In some embodiments, such as illustrated in the embodiment of FIG. 2, the seventh surface 226 may be characterized as generally convex or as having predominantly convex surface features and, likewise, the eighth surface 227 may be characterized as generally concave or as having predominantly concave surface features.

In some embodiments, for example, in the example of FIG. 2, the cover 125 and the contact layer 215 may be sized such that a peripheral portion of the cover 125 and the periphery 225 of the contact layer 215 each extend beyond the perimeter of the manifold layer 205 and the fluid management layer 210. For example, the cover 125 and the contact layer 215 may have dimensions such that a perimeter of the cover 125 is substantially coextensive with the edges 245 of the periphery 225 of the contact layer 215 when the cover 125, the manifold layer 205, the fluid management layer 210, and the contact layer 215 are positioned with respect to each other. In some embodiments, the contact layer 215 and the cover 125 may be coupled, such as via the adhesive 255, to enclose the manifold layer 205 and the fluid management layer 210, also allowing a portion of the adhesive 255 to be exposed through the apertures 235.

Figure 3:
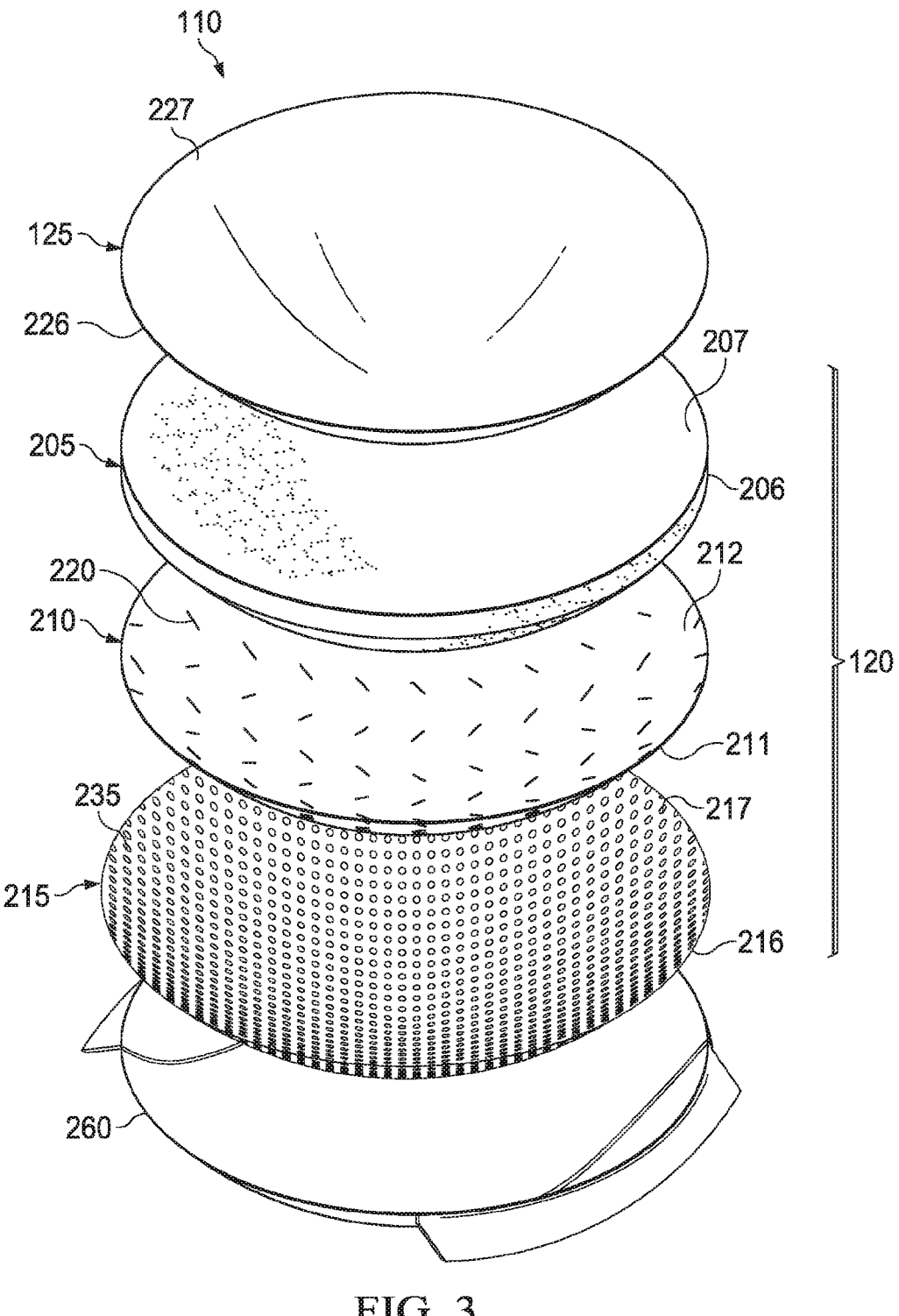
FIG. 3 is an exploded view of an example of a dressing, illustrating additional details that may be associated with some example embodiments of the therapy system of FIG. 1.

FIG. 3 is an exploded view of another example of the dressing 110 of FIG. 1, illustrating additional details that may be associated with some embodiments in which the tissue interface 120 comprises more than one layer. As similarly discussed with respect to FIG. 2, the tissue interface 120 illustrated in FIG. 3 includes a plurality of layers, more particularly, a manifold layer 205, a fluid management layer 210, and a contact layer 215. In the embodiment of FIG. 3, the cover 125, the manifold layer 205, the fluid management layer 210, and the contact layer 215 may have substantially equivalent sizes and shapes, for example, such that each of the cover 125, the manifold layer 205, the fluid management layer 210, and the contact layer 215 are coextensive with respect to an outline or perimeter when the cover 125, the manifold layer 205, the fluid management layer 210, and the contact layer 215 are disposed in a stack. Also in the embodiment of FIG. 3, each of the cover 125, the manifold layer 205, the fluid management layer 210, and the contact layer 215 may be attached, such as via an adhesive or RF welding, to an immediately-adjacent layer.

Figure 4:
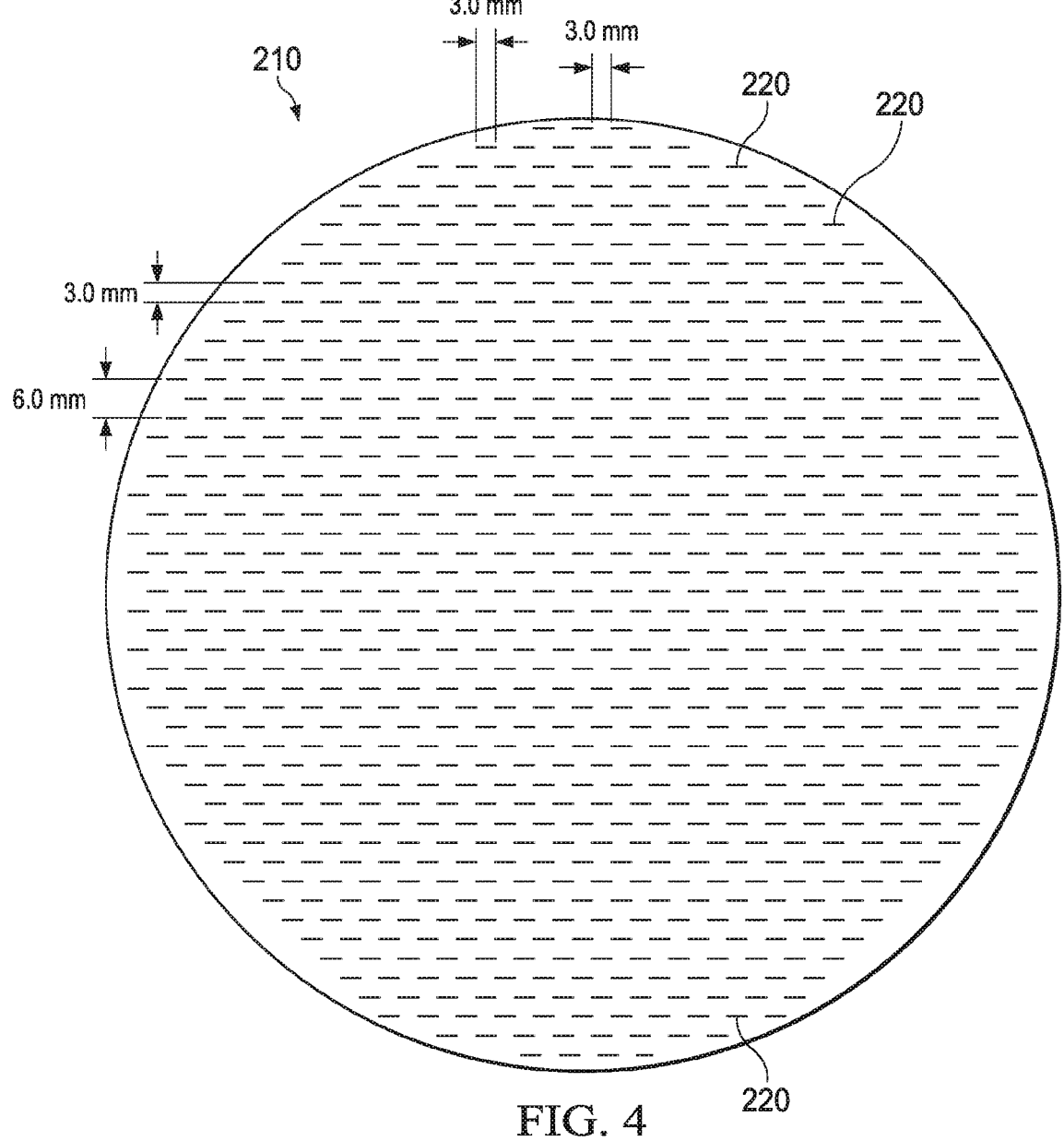
FIG. 4 is a schematic view of an example configuration of fluid restrictions in a layer that may be associated with some embodiments of a dressing.

FIG. 4 is a schematic view of an example of the fluid management layer 210, illustrating additional details that may be associated with some embodiments. As illustrated in the example of FIG. 4, the fluid restrictions 220 may each consist essentially of one or more linear slots having a length of about 3 millimeters. FIG. 4 additionally illustrates an example of a uniform distribution pattern of the fluid restrictions 220. In the embodiment of FIG. 4, the fluid restrictions 220 are substantially coextensive with the fluid management layer 210, and are distributed across the fluid management layer 210 in a plurality of parallel rows and columns, in which the slots are also mutually parallel to each other. In some embodiments, the rows may be spaced about 3 millimeters on center, and the fluid restrictions 220 within each of the rows may be spaced about 3 millimeters on center, as illustrated in the example of FIG. 4. The fluid restrictions 220 in adjacent rows may be aligned or may be offset. For example, adjacent rows may be offset, as illustrated in FIG. 4, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

Figure 5:
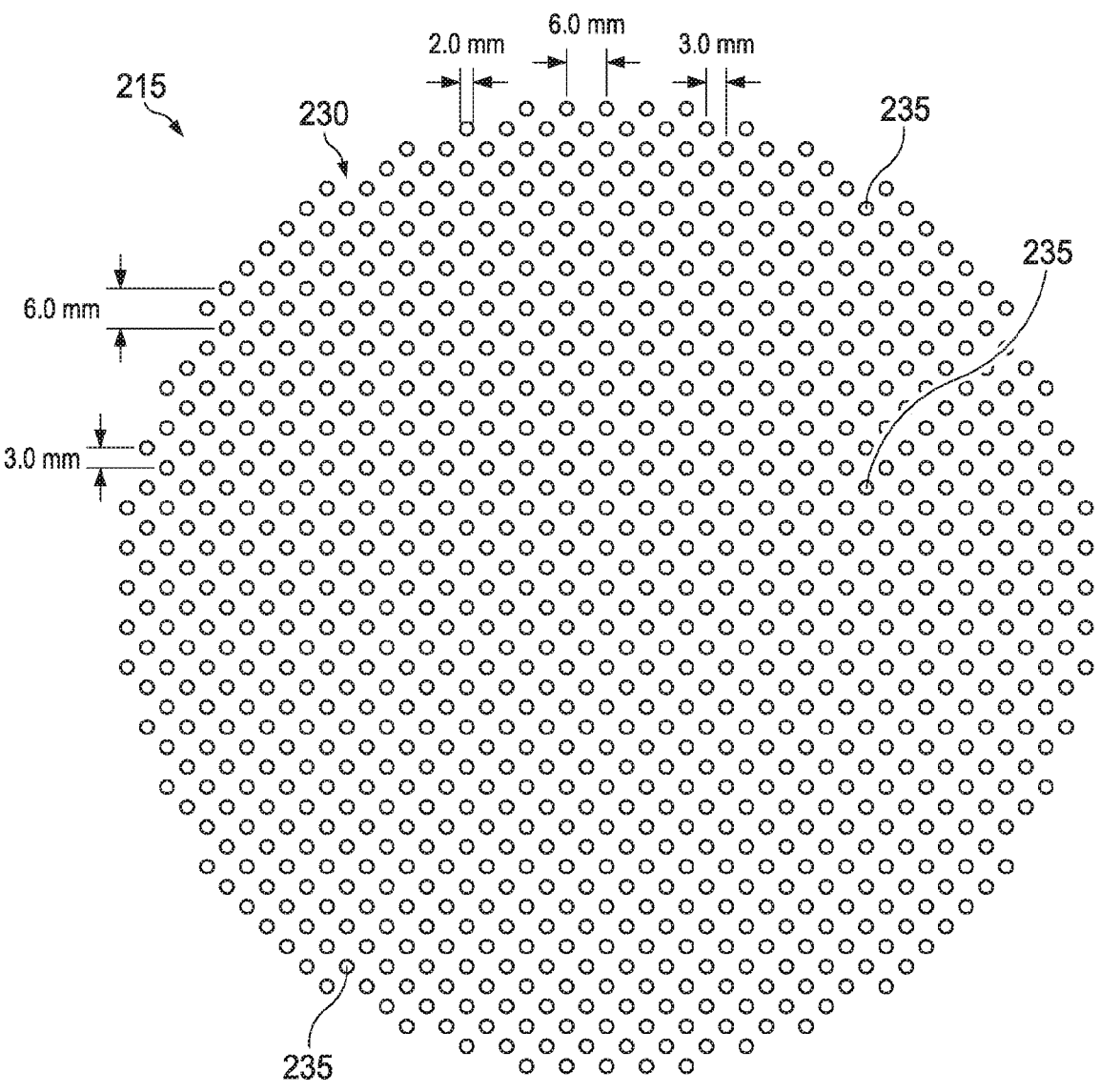
FIG. 5 is a schematic view of an example configuration of apertures in another layer, illustrating additional details that may be associated with some embodiments of a dressing.

FIG. 5 is a schematic view of an example configuration of the apertures 235, illustrating additional details that may be associated with some embodiments of the contact layer 215. In some embodiments, the apertures 235 illustrated in FIG. 5 may be associated only with the interior portion 230. In the example of FIG. 5, the apertures 235 are generally circular and have a diameter of about 2 millimeters. FIG. 5 also illustrates an example of a uniform distribution pattern of the apertures 235 in the interior portion 230. In the embodiment of FIG. 5, the apertures 235 are distributed across the interior portion 230 in a plurality of parallel rows and columns. Within each row and column, the apertures 235 may be equidistant from each other, as illustrated in the example of FIG. 5. FIG. 5 illustrates one example configuration that may be particularly suitable for many applications, in which the apertures 235 are spaced about 6 millimeters apart along each row and column, with a 3 millimeter offset.

Figure 6:
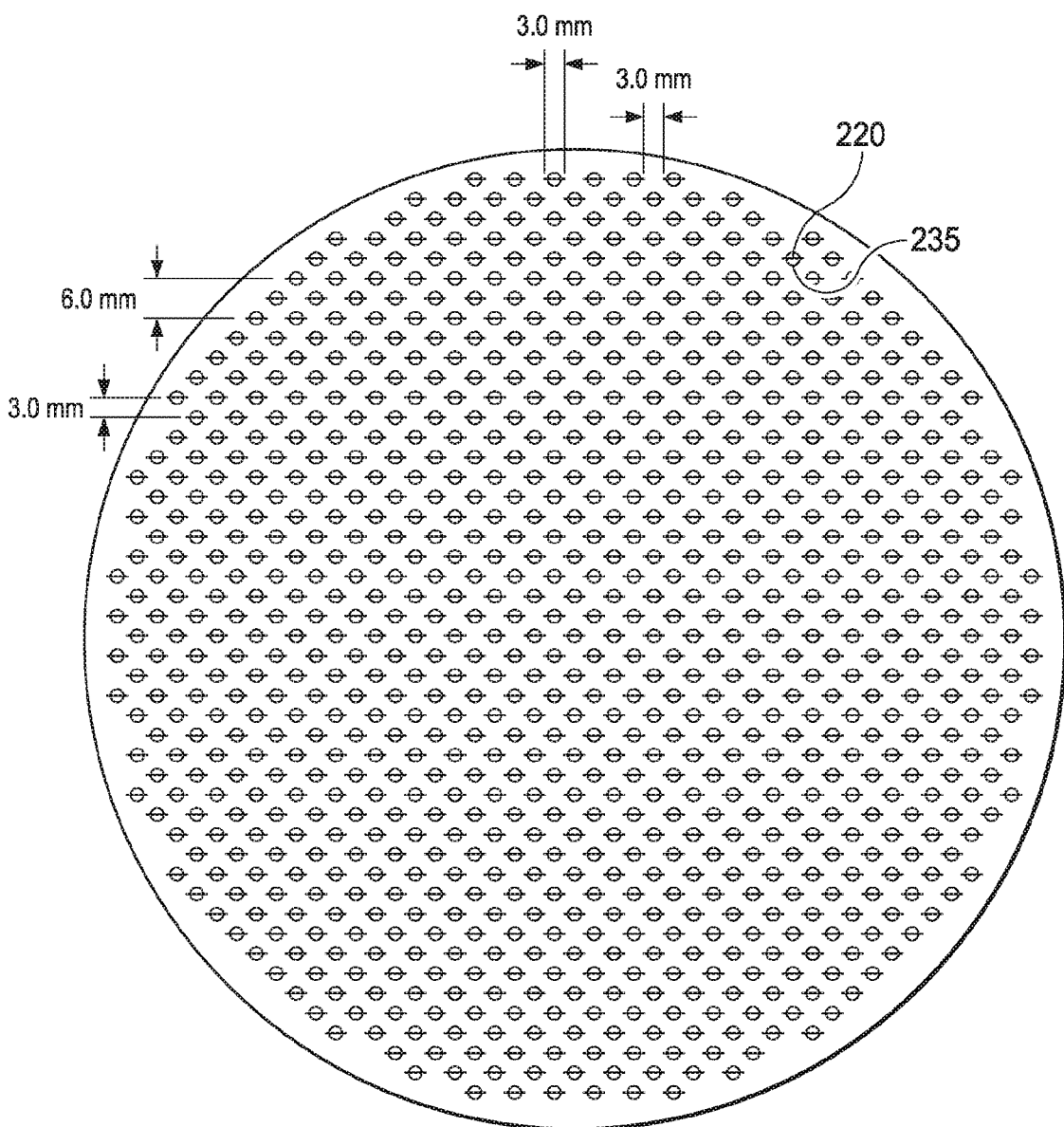
FIG. 6 is a schematic view of the example layer of FIG. 4 overlaid on the example layer of FIG. 5.

FIG. 6 is a schematic view of the example contact layer 215 of FIG. 5 overlaid on the fluid management layer 210 of FIG. 4, illustrating additional details that may be associated with some example embodiments of the tissue interface 120. For example, as illustrated in FIG. 6, the fluid restrictions 220 may be aligned, overlapping, in registration with, or otherwise fluidly coupled to the apertures 235. In some embodiments, one or more of the fluid restrictions 220 may be registered with the apertures 235 only in the interior portion 230, or only partially registered with the apertures 235. The fluid restrictions 220 in the example of FIG. 6 are generally configured so that each of the fluid restrictions 220 is registered with only one of the apertures 235. In other examples, one or more of the fluid restrictions 220 may be registered with more than one of the apertures 235. For example, any one or more of the fluid restrictions 220 may be a perforation or a fenestration that extends across two or more of the apertures 235. Additionally or alternatively, one or more of the fluid restrictions 220 may not be registered with any of the apertures 235.

As illustrated in the example of FIG. 6, the apertures 235 may be sized to expose a portion of the fluid management layer 210, the fluid restrictions 220, or both through the contact layer 215. In some embodiments, each of the apertures 235 may be sized to expose no more than two of the fluid restrictions 220. In some examples, the length of each of the fluid restrictions 220 may be substantially equal to or less than the diameter of each of the apertures 235. In some embodiments, the average dimensions of the fluid restrictions 220 are substantially similar to the average dimensions of the apertures 235. For example, the apertures 235 may be elliptical in some embodiments, and the length of each of the fluid restrictions 220 may be substantially equal to the major axis or the minor axis. In some embodiments, though, the dimensions of the fluid restrictions 220 may exceed the dimensions of the apertures 235, and the size of the apertures 235 may limit the effective size of the fluid restrictions 220 exposed to the lower surface of the dressing 110.

In some embodiments, one or more components of the dressing 110 may be subjected to a thermoforming process, for example, one or more of the cover 125, the manifold layer 205, the fluid management layer 210, and the contact layer 215 may be subjected to thermoforming to impart non-planar surface features to these components. For example, one or more of the non-planar surfaces of the tissue interface 120, for example, one or more of the first surface 206, the second surface 207, the third surface 211, the fourth surface 212, the fifth surface 216, the sixth surface 217, the seventh surface 226, and the eighth surface 227, may be formed by the thermoforming process.

In some embodiments, two or more components of the dressing 110 may be coupled together prior to the thermoforming; additionally or alternatively, in some embodiments, two or more components of the dressing 110 may be thermoformed apart from each other and then coupled together after the thermoforming. For example, in some embodiments, the cover 125, the manifold layer 205, the fluid management layer 210, and the contact layer 215 may be first coupled together and then subjected to thermoforming. Alternatively, in some embodiments, two or more of the cover 125, the manifold layer 205, the fluid management layer 210, and the contact layer 215 may be thermoformed prior to being coupled to an adjacent component of the dressing 110.

In some embodiments, the thermoforming process includes heating a precursor material to a temperature at which the precursor material becomes pliable. In various embodiments, the parameters associated with heating the precursor material may be selected based upon factors including the material being thermoformed. In some embodiments, in the context of thermoforming the manifold layer 205, the temperatures associated with the thermoforming process may generally be less than those temperatures that might be associated with a felting process by which the manifold layer 205 may become compressed.

Additionally, in some embodiments, the heated precursor material may be conformed to a form or mold, for example, a mandrel. Generally, the form to which the heated precursor material is conformed may be selected based upon the desired characteristics of the resultant component of the tissue interface 120. For example, the form may include a three-dimensional shape such as a portion of an interior or exterior surface of a sphere, an ellipsoid, a torus, a cylinder, a paraboloid, a hyperboloid, a cone, a prism, a pyramid, a tetrahedron, or combinations thereof. The heated precursor material may be conformed by any suitable methodology. For example, in some embodiments, the heated precursor material may be conformed to the form or mold by a vacuum. Additionally, in some embodiments, the heated precursor material may be cooled while conformed to the form and, upon cooling, one or more surfaces features may be imparted to one or more of the cover 125, the manifold layer 205, the fluid management layer 210, and the contact layer 215.

In some embodiments, in addition or as an alternative to imparting one or more surface features to a component of the dressing 110, the thermoforming process may also be effective to modify one or more parameters associated with the dressing 110, the tissue interface 120, or one or more components thereof, for example, the cover 125, the manifold layer 205, the fluid management layer 210, and the contact layer 215. For example, in some embodiments, the dressing 110, one or more components of the dressing 110, or some combination of the components of the dressing 110 may be characterized as exhibiting a decrease in tensile strength after the thermoforming process and/or as a result of the thermoforming process. For example, the dressing 110, one or more components of the dressing 110, or some combination of the components of the dressing 110 may be characterized as exhibiting a decrease in tensile strength in comparison to an otherwise similar dressing that has not been thermoformed. The otherwise similar dressing that has not been thermoformed may be the same as the dressing 110 in all material aspects with exception to having not undergone the thermoforming process. In some embodiments, the dressing 110, one or more components of the dressing 110, or some combination of the components of the dressing 110 may exhibit a decrease in tensile strength of at least 10% as a result of the thermoforming or in comparison to an otherwise similar dressing that has not been thermoformed, or a decrease in tensile strength of at least 15%, or a decrease in tensile strength of at least 20%, or a decrease in tensile strength of at least 25%, or a decrease in tensile strength of at least 30%, or a decrease in tensile strength of at least 35%, or a decrease in tensile strength of at least 40%.

Additionally or alternatively, in some embodiments, the dressing 110, one or more components of the dressing 110, or some combination of the components of the dressing 110 may be characterized as exhibiting increased flexure after the thermoforming process and/or as a result of the thermoforming process. For example, the dressing 110, one or more components of the dressing 110, or some combination of the components of the dressing 110 may be characterized as exhibiting increased flexure in comparison to an otherwise similar dressing that has not been thermoformed.

Additionally or alternatively, in some embodiments, the dressing 110, one or more components of the dressing 110, or some combination of the components of the dressing 110 may be characterized as exhibiting improved conformability with respect to a tissue site after the thermoforming process and/or as a result of the thermoforming process. For example, the dressing 110, one or more components of the dressing 110, or some combination of the components of the dressing 110 may be characterized as exhibiting improved conformability with respect to a tissue site in comparison to an otherwise similar dressing that has not been thermoformed.

Figure 7:
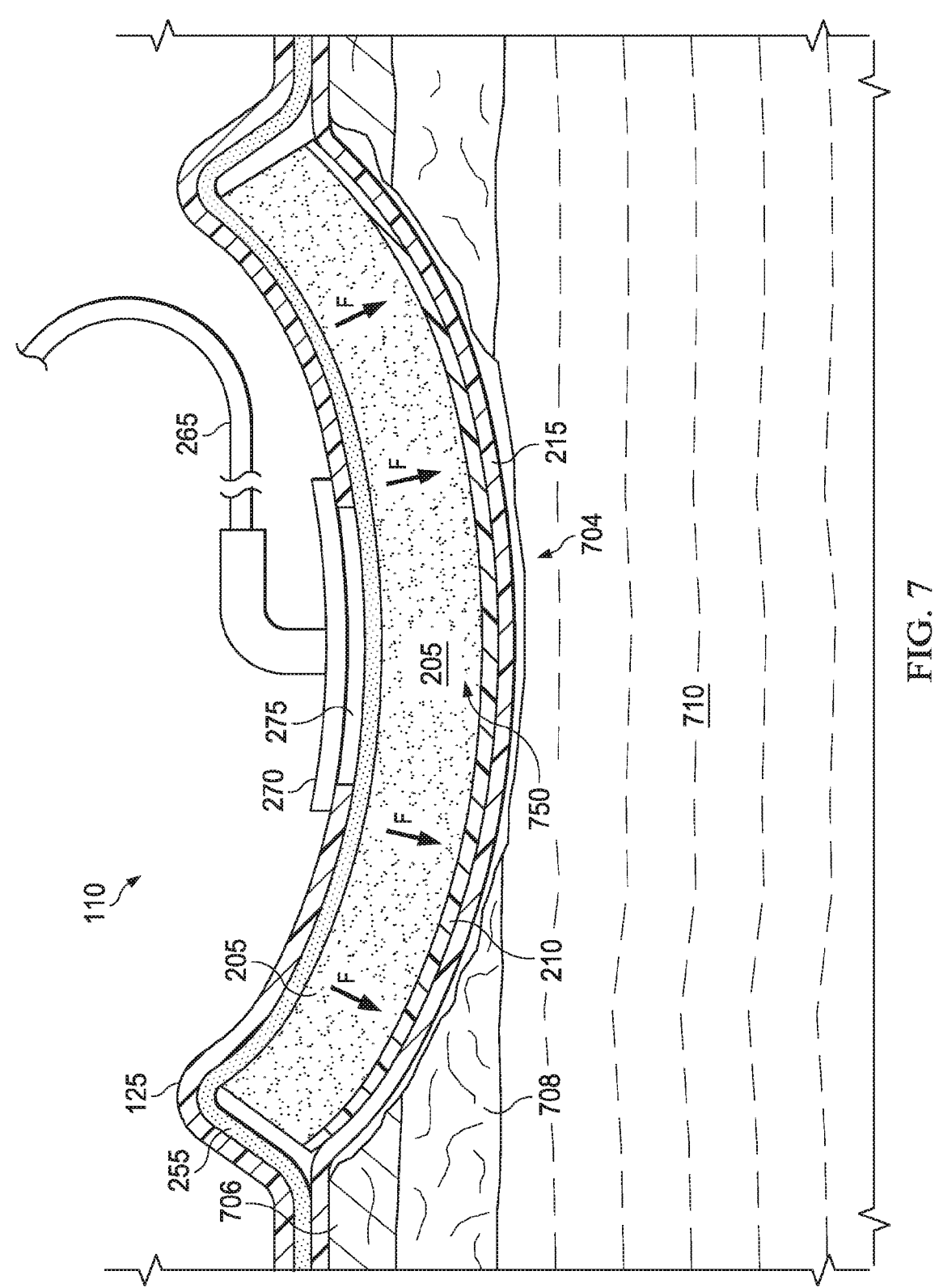
FIG. 7 is a cut-away view illustrating additional details that may be associated with some example embodiments of the dressing of FIG. 2.

For example, and not intending to be bound by theory, the increased flexure and/or the improved conformability may result from a decrease in tensile strength of the dressing 110, one or more components of the dressing 110, or some combination of the components of the dressing 110. For example, referring to FIG. 7, a cutaway view of the dressing 110 of FIG. 2 is illustrated positioned with respect to a tissue site 704 of a patient. The tissue site 704 may extend through or otherwise involve peripheral tissue, for example, an epidermis 706, a dermis 708, and a subcutaneous tissue 710. Additionally or alternatively, in some embodiments, the tissue site 704 may include a surface portion that predominantly resides on the surface of the epidermis 706, such as, for example, an incision. The tissue site 704, for example, a deep wound, may have a depth extending beneath the surface of the peripheral tissue, for example, the epidermis 706. As shown illustrated by FIG. 7, when positioned with respect to the tissue site 704, the dressing 110 may extend over the tissue site 704 such that the dressing 110 is supported about its periphery by the peripheral tissue. In some embodiments, the application of one or more forces, F, applied to the dressing 110 in the direction of the tissue site 704 (e.g., a force into the tissue site 704) may cause a region 750 of the dressing 110, one or more components of the dressing 110, or some combination of the components of the dressing 110 to experience tension. In some embodiments, a decrease in the tensile strength of the dressing 110, one or more components of the dressing 110, or some combination of the components of the dressing 110, as may result from the thermoforming process, may cause the dressing 110, one or more components of the dressing 110, or some combination of the components of the dressing 110 to exhibit increased flexure and/or improved conformability.

In some embodiments, the dressing 110 may be subjected to the thermoforming process in its entirety, for example, such that the entirety of various components of the dressing 110 may be subjected to the thermoforming process. Alternatively, in some embodiments, less than the entirety of the dressing 110 may be subjected to the thermoforming process. For example, in some embodiments, less than the entirety of one or more components of the dressing 110 may be subjected to the thermoforming process. Additionally or alternatively, in some embodiments, the dressing 110 and/or one or more components of the dressing 110 may include various regions having been subjected to varying degrees of the thermoforming process, for example, such that the dressing 110 and/or one or more components of the dressing 110 may exhibit variations in tensile strength, flexure, and/or conformability at various regions thereof. For example, in some embodiments, the dressing 110 and/or one or more components of the dressing 110 may include one or more thermoformed regions, for example, one or more tension-relief regions.

Figure 8:
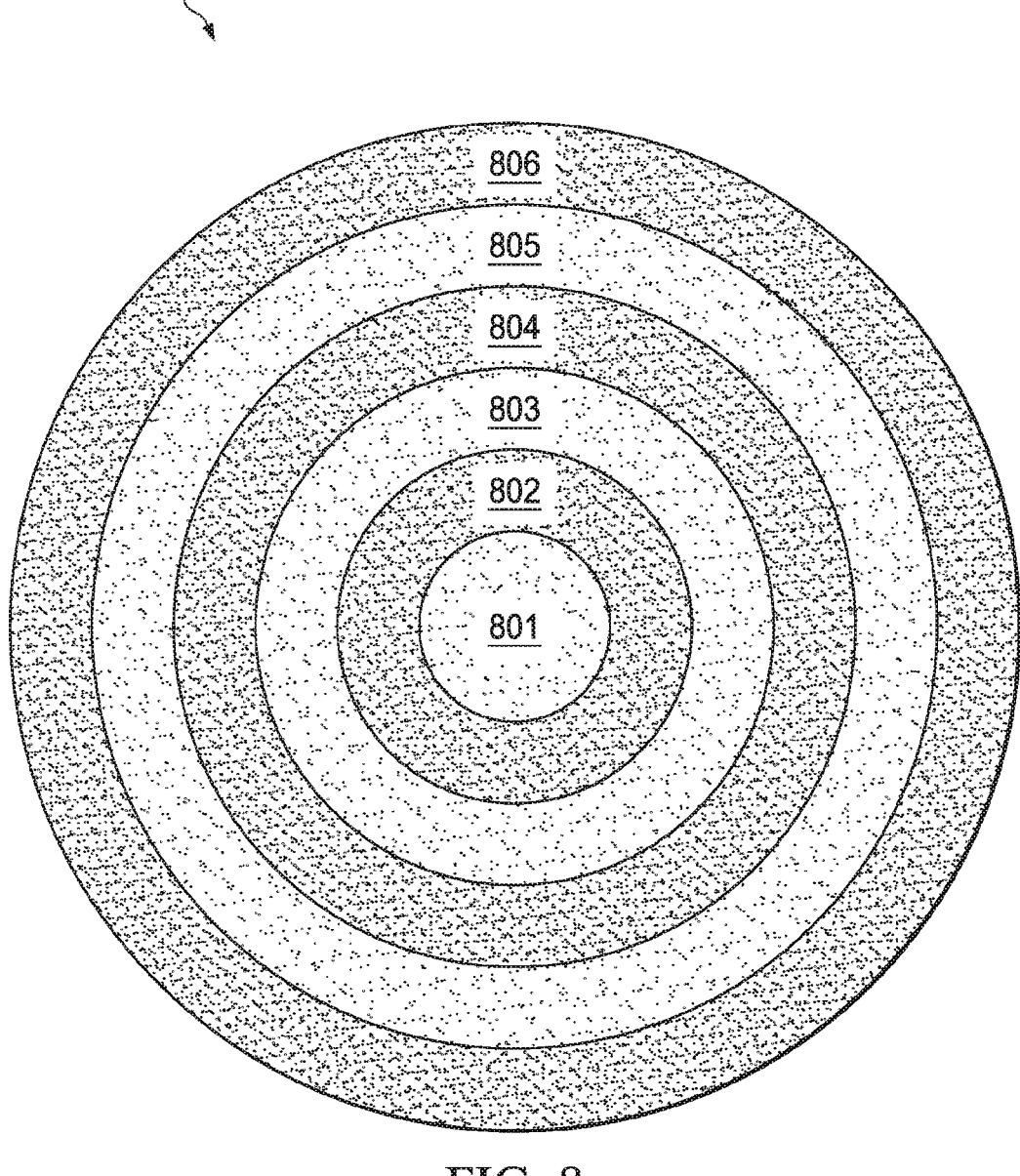
FIG. 8 is a schematic view of an example configuration of a manifold layer that may be associated with some embodiments of a dressing.

For example, referring to FIG. 8, an example embodiment of the manifold layer 205 is illustrated. In the embodiment of FIG. 8, the manifold layer 205 includes a plurality of tension-relief regions, for example, a first tension-relief region 802, a second tension-relief region 804, and a third tension-relief region 806. The manifold layer 205 may also include one or more regions exhibiting relatively little modification to the tensile strength, for example, a first low-modification region 801, a second low-modification region 803, and a third low-modification region 805. The tension-relief regions, particularly, the first tension-relief region 802, the second tension-relief region 804, and the third tension-relief region 806, may be formed by subjecting the tension-relief regions to the thermoforming process while the low-modification regions are not subjected to the thermoforming process or are subjected to a lesser degree of thermoforming.

In the example of FIG. 8, one or more of the tension-relief regions concentrically-disposed may be disposed around one or more of the low-tension-relief regions. For example, as shown in the embodiment of FIG. 8, the first tension-relief region 802 may be disposed generally concentrically around the first low-modification region 801; the second low-modification region 803 may be disposed generally concentrically around the first tension-relief region 802; the second tension-relief region 804 may be disposed generally concentrically around the second low-modification region 803; the third low-modification region 805 may be disposed around the second tension-relief region 804; and the third tension-relief region 806 may be disposed generally concentrically around the third low-modification region 805. While the example of FIG. 8 illustrates an arrangement of a plurality of tension-relief regions and low-modification regions disposed in the manifold layer 205, various other components of the tissue interface 120 or the dressing 110 may include similar arrangements of tension-relief regions and low-modification regions.

Figure 9:
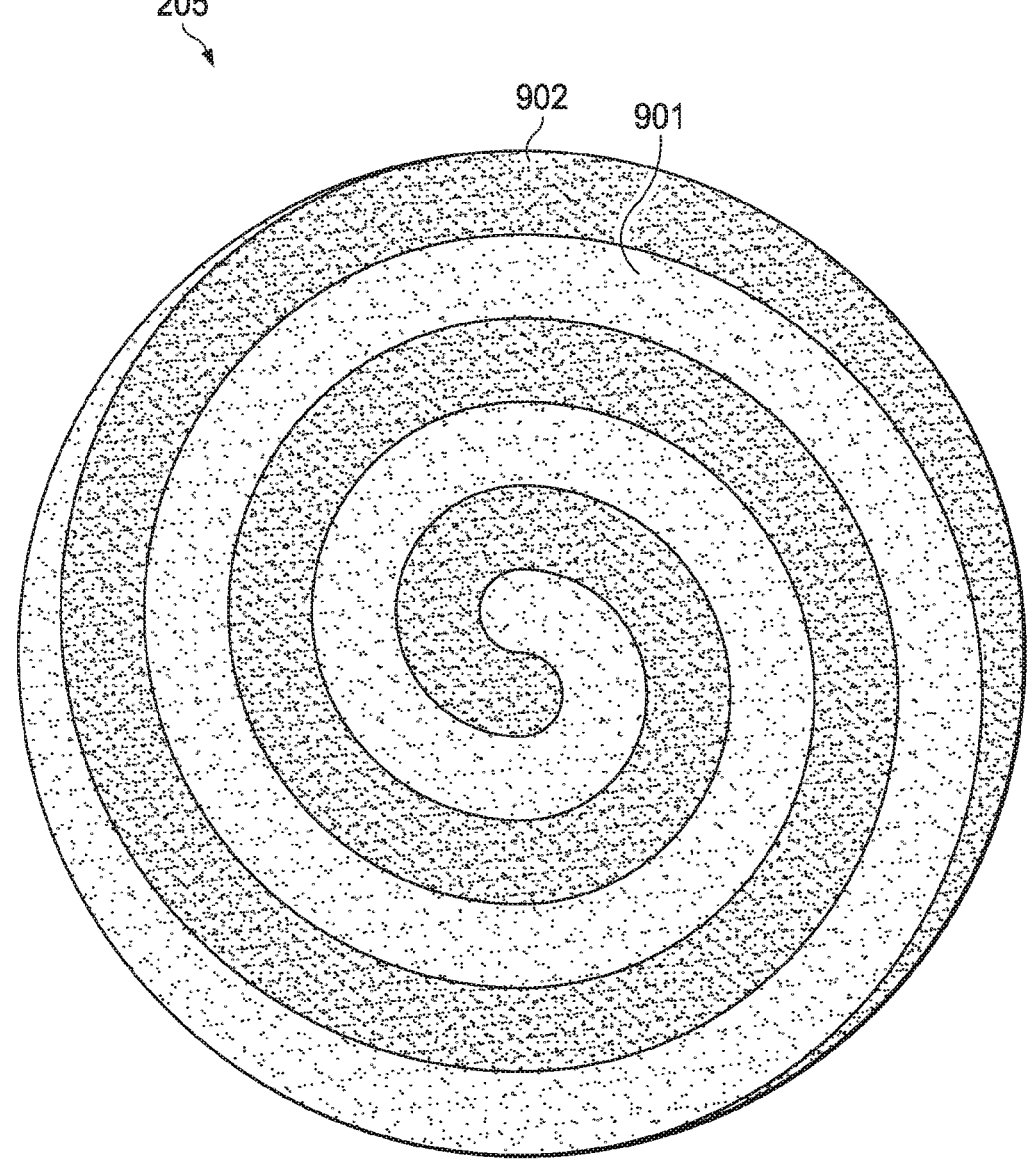
FIG. 9 is a schematic view of an example configuration of a manifold layer that may be associated with some embodiments of a dressing.

Also for example, referring to FIG. 9, another example embodiment of the manifold layer 205 is illustrated. In the embodiment of FIG. 9, the tissue interface 120 includes a spirally-shaped tension-relief region 902 and a low-modification region 901. While the example of FIG. 9 illustrates an arrangement of a plurality of tension-relief regions and low-modification regions disposed in the manifold layer 205, various other components of the tissue interface 120 or the dressing 110 may include similar arrangements of tension-relief regions and low-modification regions.

In some other example embodiments, a plurality of tension-relief regions may be disposed across the length and width of the dressing 110 and/or one or more components of the dressing 110 in any suitable pattern to yield a desired parameter. For example, in some embodiments, a plurality of tension-relief regions may be disposed in a pattern or randomly. In some embodiments, the tension-relief regions may be more concentrated in various areas where tension-relief is desired and less concentrated in areas where tension-relief is not desired or is desired to a lesser degree.

Figure 10:
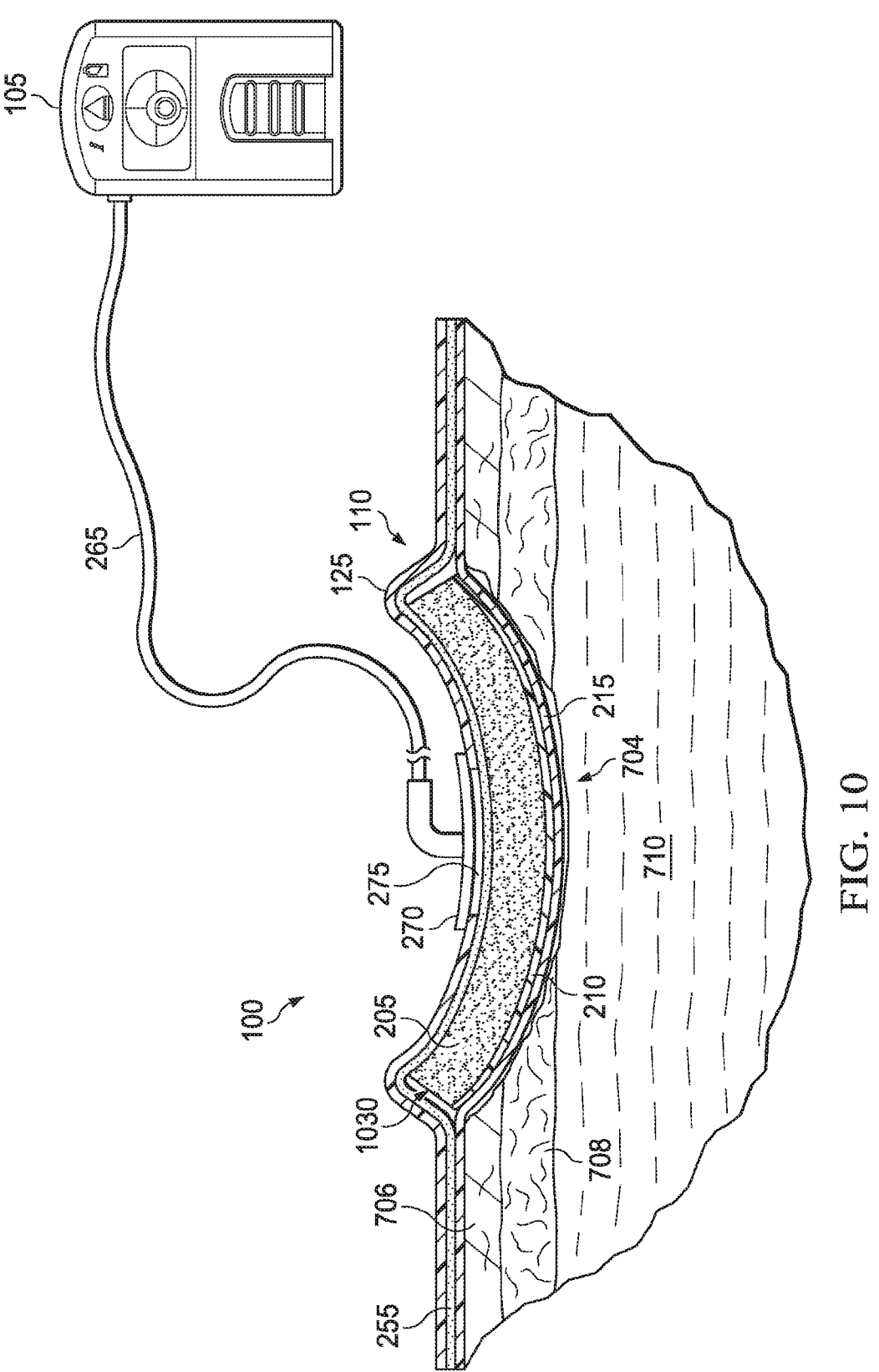
FIG. 10 is a partial cut-away view illustrating additional details that may be associated with some example embodiments of the therapy system of FIG. 1.

A system comprising the dressing 110 may be advantageously employed to provide negative-pressure therapy to a user. For example, FIG. 10 depicts an embodiment of the therapy system 100 positioned for the treatment of the tissue site 704. The therapy system 100 may provide therapy to, for example, the epidermis 706, the dermis 708, and the subcutaneous tissue 710, regardless of the positioning of the therapy system 100 or the type of tissue site. The therapy system 100 may also be utilized without limitation at other tissue sites.

The dressing 110 may be positioned with respect to the tissue site 704 such that the interior portion 230 of the contact layer 215 is positioned at or proximate to the tissue site 704, and such that the periphery 225 of the contact layer 215 is positioned proximate to peripheral tissue, for example, the epidermis 706, surrounding the tissue site 704. Further, the apertures 235 in the contact layer 215 may be in fluid communication with the tissue site 704 and/or tissue surrounding the tissue site 704.

The dressing 110 may be positioned with respect to the tissue site 704 such that the convex surfaces, for example, the first surface 206, the third surface 211, and the fifth surface 216 may face the tissue site 704. For example, the dressing 110 may be placed with respect to the tissue site 704 such that one or more non-planar surface features extend into the tissue site 704.

The cover 125 may cover the contact layer 215 and the tissue site 704 to provide a fluid seal and a sealed space 1030 between the tissue site 704 and the cover 125 of the dressing 110. Further, the cover 125 may cover other tissue, such as a portion of the epidermis 706, surrounding the tissue site 704 to provide the fluid seal between the cover 125 and the tissue site 704. In some embodiments, a portion of the periphery of the cover 125 may extend beyond the periphery 225 of the contact layer 215 and into direct contact with tissue surrounding the tissue site 704. In other embodiments, the periphery of the cover 125, for example, may be positioned in contact with tissue surrounding the tissue site 704 to provide the sealed space 1030 without the contact layer 215. Thus, the adhesive 255 may also be positioned at least between the periphery of the cover 125 and tissue, such as the epidermis 706, surrounding the tissue site 704. The adhesive 255 may be disposed on a surface of the cover 125 adapted to face the tissue site 704 and the contact layer 215.

The adhesive 255 may extend through or be pressed through one or more of the plurality of the apertures 235, for example so as to contact the epidermis 706 and secure the dressing 110 to tissue at or surrounding the tissue site 704 when the dressing 110 is positioned with respect to the tissue site 704. For example, the apertures 235 may provide sufficient contact of the adhesive 255 to the epidermis 706 to secure the dressing 110 with respect to the tissue site 704. Additionally, the configuration of the apertures 235 and the adhesive 255 may also permit release and repositioning of the dressing 110 with respect to the tissue site 704. In various embodiments, one or more of the apertures 235 may be adjusted in size and number to adjust the surface area of the adhesive 255 in fluid communication through the apertures 235, for example, for a particular application or geometry of the contact layer 215.

Alternatively, in some embodiments, for example, in embodiments such as disclosed with respect to FIG. 3, where all components of the dressing 110 are coextensive with respect to outline or perimeter, an attachment device can be disposed around the edges of the cover 125. The attachment device may comprise a strip of material, for example, a film, having sufficient width to extend between a peripheral portion of the cover 125 and tissue at or surrounding the tissue site 704, for example, so as to form the sealed space 1030. An adhesive disposed on the attachment device may be pressed onto the cover 125 and the epidermis 706 peripheral to a tissue site to fix the dressing 110 in position and to seal the exposed perimeter of the tissue interface 120.

With the dressing 110 positioned and secured with respect to the tissue site 704, a conduit may be coupled between the negative-pressure source 105 and the dressing 110 and the negative-pressure source 105 may be operated to provide negative-pressure therapy to the tissue site 704, for example, via the sealed space 1030 and/or the dressing 110. In some embodiments, the application of negative pressure to the sealed space 1030 and/or the dressing 110 may have the effect of causing a force to be applied to the dressing 110, for example, to draw the dressing 110 into the tissue site 704.

In some embodiments, the dressing 110 may be advantageously employed in the provision of negative-pressure therapy, for example, as a result of the decreased tensile strength, increased flexure, and/or improved conformability with respect to a tissue site exhibited by the dressing 110. For example, the increased flexure and/or improved conformability of the dressing 110 may allow the dressing 110 to provide better contact between the tissue site 704 and a tissue site-facing surface of the dressing 110. The improved contact between the dressing 110 and the tissue site 704 may have the effect of inducing micro-strain across substantially all of the tissue site 704, whereby cells across the tissue site 704 experience strain, improving the outcome of the negative-pressure therapy.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may also be combined or separated in various configurations for purposes of sale, manufacture, assembly, or use. In some configurations, various components, for example, the dressing 110 or the container 115, may be separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

The invention claimed is:

1. A dressing for treating a tissue site with negative pressure, the dressing having, in a relaxed state in which no external forces are applied to the dressing, both a first non-planar surface and a second non-planar surface opposite the first non-planar surface, the dressing comprising:
   a fluid management layer comprising a polymer film and a plurality of fluid restrictions extending through the polymer film and configured to deform; and
   a manifold layer coupled to the fluid management layer;
   wherein at least a portion of the dressing comprises one or more tension-relief regions having a decreased tensile strength relative to another portion of the dressing, and wherein the one or more tension-relief regions include a non-planar surface feature.

2. The dressing of claim 1, wherein the dressing comprises a length, a width, and a thickness, wherein the thickness is substantially uniform.

3. The dressing of claim 1, wherein each of the first non-planar surface and the second non-planar surface deviates from planar by at least 50% of a thickness of the dressing.

4. The dressing of claim 1, wherein each of the first non-planar surface and the second non-planar surface deviates from planar by at least a thickness of the dressing.

5. The dressing of claim 1, wherein at least one of the first non-planar surface and the second non-planar surface comprises the non-planar surface feature, wherein the non-planar surface feature comprises at least a portion of a surface of a sphere, an ellipsoid, a torus, a cylinder, a paraboloid, a hyperboloid, a cone, a prism, a pyramid, or a tetrahedron.

6. The dressing of claim 1, wherein the dressing is formed by a thermoforming process comprising heating the fluid management layer and the manifold layer and, while heated, conforming the fluid management layer and the manifold layer to a form, wherein the first non-planar surface and the second non-planar surface are formed as a result of the thermoforming process.

7. The dressing of claim 6, wherein at least a portion of the dressing exhibits a decrease of at least 10% in tensile strength after the thermoforming process.

8. The dressing of claim 6, wherein the dressing exhibits an increase in conformability with respect to the tissue site after the thermoforming process.

9. The dressing of claim 1, wherein the first non-planar surface is a surface of the fluid management layer and comprises a convex surface, and wherein the second non-planar surface is a surface of the manifold layer and comprises a concave surface.

10. The dressing of claim 1, further comprising a polymeric layer coupled to the manifold layer opposite the fluid management layer, wherein the second non-planar surface is a surface of the polymeric layer and comprises a concave surface.

11. The dressing of claim 10, wherein the dressing is formed by a thermoforming process comprising heating the fluid management layer, the manifold layer, and the polymeric layer.

12. The dressing of claim 1, wherein the one or more tension-relief regions are thermoformed.

13. The dressing of claim 1, wherein the non-planar surface feature comprises at least a portion of a surface of a sphere, an ellipsoid, a torus, a cylinder, a paraboloid, a hyperboloid, a cone, a prism, a pyramid, or a tetrahedron.

14. The dressing of claim 1, wherein a first tension-relief region is disposed concentrically around a second tension-relief region.

15. A system for treating a tissue site, the system comprising:
   the dressing according to claim 1; and
   a negative-pressure source configured to be fluidly coupled to the dressing.

16. A method of treating a surface wound with negative pressure, the method comprising:
   applying the dressing of claim 1 to the surface wound;
   sealing the dressing to epidermis adjacent to the surface wound;
   fluidly coupling the dressing to a negative-pressure source; and
   applying negative pressure from the negative-pressure source to the dressing.

17. The method of claim 16, wherein the first non-planar surface is a surface of the fluid management layer and comprises a convex surface, wherein the dressing is applied to the surface wound such that the convex surface faces the surface wound, and wherein the convex surface extends into the wound prior to applying negative pressure.

18. A method for forming a dressing for treatment of a tissue site with negative pressure, the dressing comprising a fluid management layer comprising a polymer film and a plurality of fluid restrictions extending through the polymer film and configured to deform and also comprising a manifold layer coupled to the fluid management layer, the method comprising:
   heating the fluid management layer and the manifold layer; and
   while heated, conforming the fluid management layer and the manifold layer to a form,
   wherein the method imparts to the dressing, in a relaxed state in which no external forces are applied to the dressing, both a first non-planar surface and a second non-planar surface opposite the first non-planar surface.

19. A dressing for treating a tissue site with negative pressure, the dressing comprising:
   a first non-planar surface;
   a second non-planar surface opposite the first non-planar surface;
   a fluid management layer comprising a polymer film and a plurality of fluid restrictions extending through the polymer film and configured to deform; and
   a foam manifold layer coupled to the fluid management layer,
   wherein the first non-planar surface is a surface of the fluid management layer and comprises a convex surface, and wherein the second non-planar surface is a surface of the manifold layer and comprises a concave surface, and wherein at least a portion of the dressing exhibits a decrease in tensile strength.

20. The dressing of claim 19, wherein each of the first non-planar surface and the second non-planar surface deviates from planar by at least 50% of a thickness of the dressing.

21. The dressing of claim 19, wherein at least one of the first non-planar surface and the second non-planar surface comprises at least a portion of a surface of a sphere, an ellipsoid, a torus, a cylinder, a paraboloid, a hyperboloid, a cone, a prism, a pyramid, or a tetrahedron.

22. The dressing of claim 19, wherein the dressing exhibits an increase in conformability with respect to the tissue site.

23. A method for forming a dressing for treatment of a tissue site with negative pressure, the dressing comprising a fluid management layer comprising a polymer film and a plurality of fluid restrictions extending through the polymer film and configured to deform and also comprising a manifold layer coupled to the fluid management layer, the method comprising:

heating the fluid management layer and the manifold layer; and while heated, conforming the fluid management layer and the manifold layer to a form, wherein at least a portion of the dressing exhibits a decrease in tensile strength after the thermoforming process.

* * * * *